United States Patent
Nakamura et al.

(12) 
(10) Patent No.: US 6,205,862 B1
(45) Date of Patent: Mar. 27, 2001

(54) VISCOELASTICITY MEASUREMENT APPARATUS

(75) Inventors: Nobutaka Nakamura; Haruo Takeda; Masafumi Take, all of Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/199,239

(22) Filed: Nov. 24, 1998

(30) Foreign Application Priority Data

Nov. 25, 1997 (JP) .................................................... 9-323570

(51) Int. Cl.[7] ........................................................ G01N 3/00
(52) U.S. Cl. ................................................. 73/796; 73/808
(58) Field of Search ............................. 73/788, 789, 805, 73/806, 811, 796, 808

(56) References Cited

U.S. PATENT DOCUMENTS

| | | | |
|---|---|---|---|
| 3,699,808 | * 10/1972 | Ford et al. | 73/772 |
| 4,719,804 | * 1/1988 | Maruyama | 73/794 |
| 4,967,601 | 11/1990 | Teramoto | 73/789 |
| 5,182,950 | 2/1993 | Takeda | 73/811 |
| 5,287,749 | 2/1994 | Nakamura | 73/808 |

FOREIGN PATENT DOCUMENTS

| | | |
|---|---|---|
| 2238879 | 2/1979 | (DE) . |
| 3240666 | 5/1984 | (DE) . |
| 4306119 | 9/1994 | (DE) . |
| WO9102235 | 2/1991 | (WO) . |

OTHER PUBLICATIONS

Patent Abstracts of Japan, vol. 006, No. 034 (P–104) Mar. 2, 1982.

* cited by examiner

*Primary Examiner*—Max Noori
(74) *Attorney, Agent, or Firm*—Adams & Wilks

(57) ABSTRACT

A viscoelasticity measurement instrument having a support whose position can be varied relative to a sample holder for holding an end portion of a sample. A detection rod is resiliently held to the support, and holds a part of the sample. When a DC or AC force is applied to the detection rod, the displacement of the detection rod relative to the support is detected. The position of the support is varied or the DC force is varied to restore the displacement to zero. In this manner, the effect of the elastic constant of the support is eliminated. In one embodiment, a detection rod is support by leaf springs. Negative feedback control is utilized to return deformation of the leaf springs to zero at all times to eliminate the spring constant effect of the leaf springs. Since the average displacement of the leaf springs is zero, the positional relation between the permanent magnet and the coil forming the electromagnetic force generator varies negligibly. Therefore, the linearity between the current flowing through the coil and the generated force is secured well to enhance the accuracy of the measured viscoelasticity data.

24 Claims, 6 Drawing Sheets

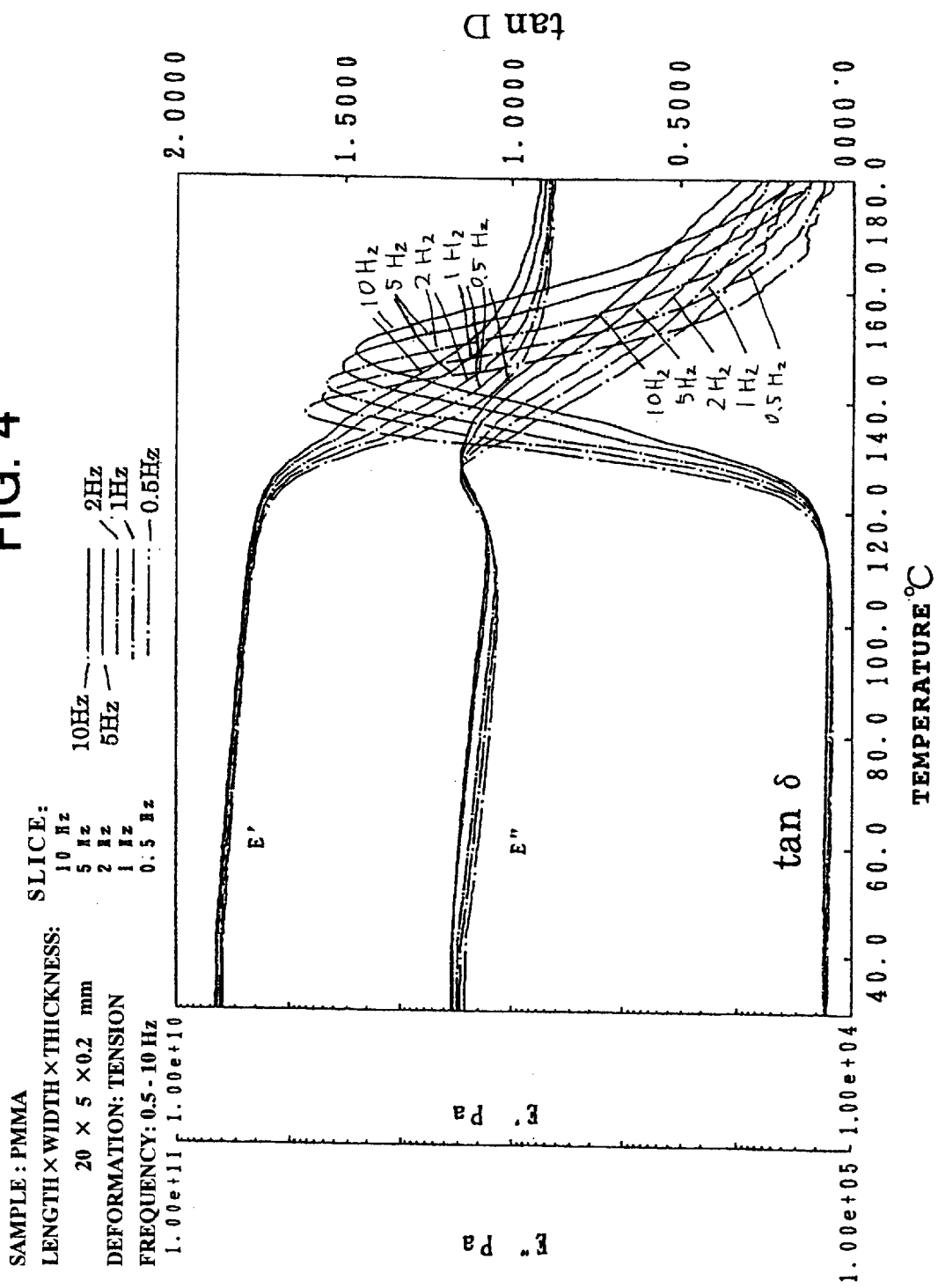

VISCOELASTICITY MEASUREMENT APPARATUS

BACKGROUND OF THE INVENTION

The present invention relates to an instrument for measuring the static viscoelasticity and/or dynamic viscoelasticity of a material.

A known invention of this kind is an instrument for measuring the relation between the stress and strain in a material as described in Patent Publication No. 57-40963 (hereinafter referred to as the first prior art). Also, as described in Patent Laid-Open No. 63-139232 (hereinafter referred to as the second prior art instrument), an improved instrument is available. The mechanisms of this instrument are simplified to increase the mechanical strength and to decrease the weight of the vibrating system. Thus, the effects of the mechanical resonance are mitigated. Hence, the dynamic viscoelasticity of the material can be measured. In addition, as described in Patent Laid-Open No. 3-82934 (hereinafter referred to as the third prior art instrument), another improved instrument applies an alternating force to a material. A DC current is added to the alternating force. The DC strain component of the strain developed in the material is mechanically compensated. The dynamic viscoelasticity of the material can be measured only from the AC component by the pulling system.

In all of these prior art instruments, a force is applied to a sample via a detection rod. The strain in the sample is detected by a displacement detector placed between the detection rod and an external support. The detection rod of these instruments needs to be supported by a support within the instrument of some form. In the first prior art instrument, a balance support mechanism is used. In the second and third prior art instruments, leaf springs are mounted to the supports.

In each prior art instrument described above, the friction between the detection rod and the support must be small (i.e., the viscous resistance between the detection rod and the support is small). This is a characteristic generally required for each system for holding the detection rod.

In addition, in order to measure the static viscoelasticity of the sample, the elastic coupling constant (spring constant) between the detection rod and the support) is required to be small.

To measure the dynamic viscoelasticity of a sample, the mass of the vibrating portion including the detection rod must be small, forminimizing the measurement error due to inertia. Furthermore, the resonant frequency of the vibrating portion determined by the ratio of the elastic coupling constant to the mass of the vibrating portion needs to be higher than the measured frequency and so it is necessary that the elastic coupling constant between the detection rod supports be considerably large.

In particular, measurement of the static viscoelasticity of a sample and measurement of the dynamic viscoelasticity are common in that the relation between a stress and a strain produced in the sample is measured. However, where the detection rod is held as in the prior art technique described above, conflicting requirements take place concerning the elastic coupling constant between the detection rod and the support. Consequently, any instrument capable of accurately measuring both static and dynamic viscoelasticities of a sample has not existed.

In practice, the static viscoelasticity can be measured, using the first prior art instrument. However, measurement of the dynamic viscoelasticity is limited to quite low frequencies of less than 1 Hz due to the large mass of the balance mechanism.

On the other hand, in the second and third prior art instruments, it is possible to measure dynamic viscoelasticity up to higher frequencies such as hundreds of Hz. In measuring the static viscoelasticity of a sample, it is difficult to separate the contribution of the spring constant of leaf springs when the stress and strain vary at the same time.

In consequence, sufficient measuring accuracy cannot be obtained.

SUMMARY OF THE INVENTION

The present invention has been developed to solve the problems described above. The invention comprises:a sample holder for supporting at least one end of a sample; a sample chuck for supporting a part of said sample; a detector support capable of moving relative to said sample holder; a detection rod coupled to said sample chuck and elastically held to said detector support; a displacement detector for sensing variations in longitudinal position of said detection rod relative to said detection support; a force generator fixedly mounted to said detection support and acting to apply a longitudinal force to one end of said detection rod to thereby apply stress to said sample via said detection rod and via said sample chuck; a function generator connected with said force generator and acting to establish a DC component and an AC component of a stress applied to the sample; a mechanical feedback control means for varying the position of said detector support relative to said sample holder so that a DC component output from said displacement detector approaches zero; negative feedback control means for varying the DC output from said force generator so that the DC component output from said displacement detector approaches zero; recording means for recording the output from said force generator and amount of movement of said detector support relative to said sample holder; and an arithmetic unit for Fourier-transforming periodic function components of the periodic function signal from said periodic function generator and periodic function components of a displacement signal sensed by said displacement detector.

In the operation of the structure described above, at least one of a DC force and an AC force is applied to the sample via the detection rod from the force-generating portion. The sample is held to the sample holder and to the sample chuck. At this time, reflecting the linear viscoelasticity between the sample and the elastic support, a DC-like strain is induced in the DC force, and an AC-like strain is induced in the AC force. Both are sensed by the displacement detector.

The AC-like strain sensed by the displacement detector is compared with the applied AC force and is thus detected as a composite dynamic viscoelasticity of both sample and elastic support. If the sample and the elastic support are coupled parallel, the dynamic viscoelasticity of the sample can be determined by subtracting the elastic modulus of the elastic support from the composite dynamic viscoelasticity.

The applied DC force and the DC component of strain sensed by the displacement detector can be measured by passing the displacement signal through a low-pass filter or continuously applying DC waves and intermittently applying AC waves and then measuring the displacement when no AC wave is applied. At this time, the detector support is moved or the DC force is varied according to the measured value so that the measured value of the DC component of the displacement signal approaches zero. At this time, the amount of movement of the detector support represents the deformation of the sample. The elastic support is not deformed. Accordingly, the applied DC force is fully distributed to the sample. That is, the applied DC force and the amount of movement of the detector support represent the static stress and the static strain, respectively, in the sample oand, therefore, the static viscoelasticity of the sample can be measured.

BRIEF DESCRIPTION OF THE DRAWINGS

FIG. 3a is a cross section illustrating a sample-holding structure for holding a sample in compression; FIG. 3b is a cross section illustrating a sample-holding structure for bending a sample at three points; FIG. 3c is a cross section illustrating a sample-holding structure for holding a sample in dual cantilever; FIG. 3d is a cross section illustrating a sample-holding structure for holding a sample in single cantilever; and FIG. 3e is a cross section illustrating a sample-holding structure for holding a sample in such a way that a shear occurs;

FIG. 4 is data obtained by measuring the dynamic viscoelasticity of PMMA (polymethyl methacrylate), using composite wave;

DETAILED DESCRIPTION OF THE INVENTION

Figure 1:
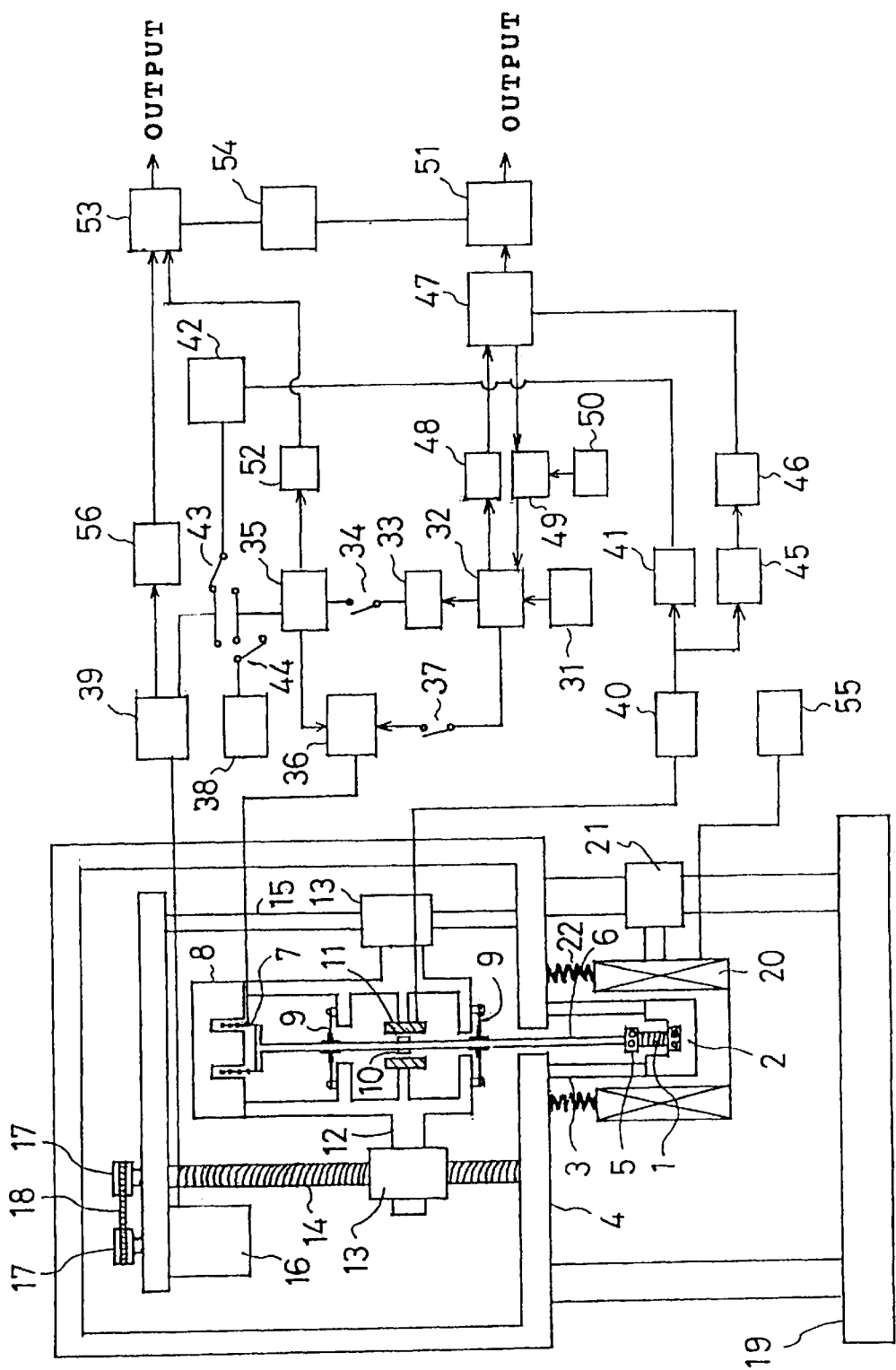
FIG. 1 is a cross-sectional view partially in block diagram showing one embodiment of the present invention.

The present invention is hereinafter described in detail by referring to the drawings given in the illustrative embodiments.

In FIG. 1, 1 is a sample having one end fixedly held to a sample holder 2 via a screw 2a. The sample holder 2 is mounted to the external underside of a detector box 4 by a pillar 3. The other end of the sample 1 is gripped by a chuck 5, which is mounted to one lower end of a detection rod 6 placed vertically. The manner in which the sample 1 is mounted to the sample holder 2 and to the chuck 5 is not limited to the embodiment described above. Depending on the purpose of the measurement, the sample may be simply supported.

The detection rod 6 extends vertically through a hole formed in the bottom of the detector box 4. A coil 7 is mounted to the upper, other end of the detection rod 6. A permanent magnet 8 mounted to a detector support 12 is arranged around the coil 7. When the coil 7 is electrically energized, it cooperates with the permanent magnet 8, exerting a force on the detection rod 6 longitudinally. That is, the coil 7 and the permanent magnet 8 together form an electromagnetic force-generating device for applying an axial force to the detection rod 6.

The detection rod 6 is resiliently held to the detection support 12 by two leaf springs 9 to permit the detection rod 6 to move only in the longitudinal direction. The two leaf springs 9 allow the detection rod 6 to move in the longitudinal direction (axial direction), and limit radial movement of the detection rod 6. The two leaf springs 9 and the detection rod 6 may be detachably or slidably mounted.

A core 10 is mounted to a part of the detection rod 6 between the two leaf springs 9. The core 10 is disposed inside the detector box 4. A linear variable differential transformer 11 is disposed around the core 10 such that a gap is left therebetween. The linear variable differential transformer 11 is fixedly held to the detector support 12 and detects relative displacement of the core 10 as a strain in the sample 1. That is, the core 10 and the working transformer 11 constitute a strain detector for detecting strain. Bearings 13 permit the detector support 12 to engage a ball screw 14 and a guide rod 15 axially movably. The ball screw 14 and the guide rod 15 are parallel to the detector box 4 and vertically held to the detector box 4. Indicated by 16 is a stepping motor mounted to the detector box 4. Pulleys 17 are mounted to the shaft of the stepping motor 16 and the front end of the ball screw 14, respectively. A driving belt 18 is trained between the pulleys 17. As the stepping motor 16 turns, the pulleys 17 and the driving belt 18 move, rotating the ball screw 14. This can move the detector support 12 vertically while maintaining its horizontal posture via the bearings 13. That is, the coil 7, the linear variable differential transformer 11, and the leaf springs 9 can be caused to move the same distance vertically at the same time.

The detector box 4 is supported by a support mechanism 19 and has a bottom provided with a hole to pass the detection rod 6. A heating-and-cooling furnace 20 is disposed around the sample 1 to vary the temperature of the sample 1. The heating-and-cooling furnace 20 is mounted to the support mechanism 19 via a moving mechanism 21, which is capable of moving the heating-and-cooling furnace 20 up and down. The heating-and-cooling furnace 20 can vary the temperature of the sample 1 in accordance with an arbitrary temperature program. A tubular bellows 22 is inserted between the external underside of the detector box 4 and the top end portion of the heating-and-cooling furnace 20. The bottom end of the detector box 4 is securely mounted to the top end portion of the tubular bellows 22. A substantially closed space is formed inside an instrument consisting of the detector box 4, the tubular bellows 22, and the heating-and-cooling furnace 20 by elevating the furnace 20. Small holes are formed in the tubular bellows 22 to permit introduction and discharge of gas. If necessary, the sample 1 is placed in a nitrogen ambient, for example, by supplying gas into the bellows through the holes. A gap is created between the top end portion of the heating-and-cooling furnace 20 and the lower end portion of the tubular bellows 22 by moving the furnace 20 downward. Thus, the sample 1 can be withdrawn and replaced.

Indicated by numeral 31 is an AC function generator acting to set the waveform (e.g., sinusoidal wave) and the frequency of an AC force generated by an electromagnetic force generator formed by the permanent magnet 8 and the coil 7 and to produce a signal of that waveform. An amplifier 32 is connected with the AC function generator 31 to set and amplify the amplitude of the AC force.

An optimum DC value-calculating unit 33 is connected with the amplifier 32. A DC voltage generator 35 is connected with the optimum DC value-calculating unit 33 via a switch 34, and establishes the DC force generated by the electromagnetic force generator. An adder 36 is connected with the DC voltage generator 35. The amplifier 32 is also connected with the adder 36 via a switch 37. When the switch 37 is closed, the adder 36 produces a DC voltage on which an AC current is superimposed. The coil 7 is connected with the adder 36. A force is generated by the coil 7 according to the output from the adder 36. A stress is applied to the sample 1 via the detection rod 6.

A strain produced in response to the stress applied to the sample 1 is detected as a displacement of the detection rod 6 by the linear variable differential transformer 11 and sent to a strain-measuring circuit 40. A signal indicating the strain of the sample 1 measured by the strain-measuring circuit 40 is divided and passed through a low-pass filter 41 and a high-pass filter 45 connected with the strain-measuring circuit 40. Then, signals are extracted. The low-frequency component passed through the low-pass filter 41 is sent to a strain potential control circuit 42. The AC component passed through the high-pass filter 45 is sent to a Fourier-calculating unit 47 via an analog-to-digital converter 46.

An AC signal produced by the aforementioned amplifier 32 and indicating the stress in the sample 1 is sent to the Fourier-calculating unit 47 via an analog-to-digital converter 48. The Fourier-calculating unit 47 calculates the amplitude of the strain in the sample 1, the stress-strain amplitude ratio, and the stress-strain phase difference, and produces outputs. A strain amplitude controller 49 is connected with the Fourier-calculating unit 47 to send a signal obtained by measuring the strain amplitude to the strain amplitude controller 49. A target strain amplitude input device 50 is connected with the strain amplitude controller 49. The ratio of the measured signal of the strain amplitude sent from the Fourier-calculating unit 47 to the target value of the strain amplitude sent from the target strain amplitude input device 50 is calculated. The gain of the amplifier 32 is varied by a factor that is the reciprocal of the calculated ratio. That is, the strain amplitude controller 49 sets the value of the amplifier 32 in such a way that the strain amplitude of the sample 1 becomes the target amplitude.

The stress-strain amplitude ratios and the data about the phase differences calculated by the Fourier-calculating unit 47 are sent to a dynamic viscoelasticity-calculating unit 51, which determines the dynamic viscoelasticity of the sample 1, using information about the sample shape as well.

Indicated by 38 is a function generator permitting the operator to establish a desired function with time. Indicated by 39 is a stepping motor driver circuit for driving the stepping motor 16.

The strain potential control circuit 42 described above is connected with one of the stepping motor driver circuit 39 and the DC voltage generator 35 by the action of a switch 43. The function generator 38 can be switched by the action of a switch 44 among three states in which the generator is connected with the DC voltage generator 35, with the stepping motor driver circuit 39, and with nothing, respectively.

The stepping motor driver circuit 39 is connected with a static viscoelasticity-calculating unit 53 via an analog-to-digital converter 56. The DC voltage generator 35 is also connected with the static viscoelasticity-calculating unit 53 via an analog-to-digital converter 52. The calculating unit 53 calculates the stress applied to the sample 1 based on the output of the DC voltage generator 35, taking into account information regarding the shape of the sample. The calculating unit 53 calculates the strain in the sample 1 from the output from the stepping motor driver circuit 39 and determines the static viscoelasticity of the sample 1.

The viscoelasticity signals about the sample I calculated by the dynamic viscoelasticity-calculating unit 51 and the static viscoelasticity-calculating unit 53 can be stored in a storage device 54 and delivered to a recording means or display means such as a printer (not shown) or a CRT (not shown).

The operation of the instrument in accordance with the present embodiment is hereinafter described.

FIG. 1 shows the configuration of gripping of a sample in the case of a tensile measurement. First, the operation of the instrument during tensile measurement is described.

First, the operator operates the moving mechanism 21 to lower the heating-and-cooling furnace 20. The sample 1 is gripped or supported by the sample holder 2 and the chuck 5. Then, the heating-and-cooling furnace 20 is elevated and the sample 1 is placed in position in the instrument. The operator can load a desired temperature program into a temperature controller 55. In this way, the temperature of the sample 1 can be varied, or a measurement can be performed while maintaining a certain temperature.

Then, a desired measurement mode is selected for dynamic viscoelasticity measurement using sinusoidal waves, dynamic viscoelasticity measurement using composite waves, creep measurement using stress control, and stress relaxation measurement using strain control.

If measurement using sinusoidal waves is selected, the switches 34 and 37 are closed. The switch 43 connects the strain potential control circuit 42 with the stepping motor driver circuit 39. The switch 44 disconnects the function generator 38 from others. The operator sets the AC function generator 31 at a measured frequency between 0.01 Hz and 100 Hz. A target value of the strain amplitude is entered into the target strain amplitude input device 50. A DC force larger than the AC force by several percent is added to the optimum DC value-calculating unit 33 to prevent the sample from loosening or being stretched excessively. Alternatively, a DC force greater than the AC force by several grams is added. In this way, measurement conditions are established. If plural measured frequencies are established, the measured frequency is switched between these frequencies and the measurement is performed at every established frequency.

If the operator gives a MEASUREMENT START instruction to the instrument, the linear variable differential transformer 11 detects strain in the leaf springs 9. The detected strain signal is sent to the strain detection circuit 40. The low-frequency component of the strain is sent to the strain potential control circuit 42 via the low-pass filter 41. The strain potential control circuit 42 calculates the amount of movement for driving the stepping motor 16 to bring the measured strain low-frequency component close to zero at all times, based on proportional control. Then, the calculated driving amount signal is sent to the stepping motor driver circuit 39 via the switch 43. The whole instrument provides negative feedback control to move the detector support 12 up and down, thus returning the output from the linear variable differential transformer 11 to zero at all times. At this time, the low-frequency strain is always removed from the leaf springs 9. Therefore, the low-frequency component of the force generated by the electromagnetic force generator formed by the permanent magnet 8 and the coil 7 is completely at balance with the low-frequency component of the strain induced in the sample 1.

The AC function generator 31 produces a sinusoidal wave of a given frequency, which is amplified by the amplifier 32 and sent to the adder 36 via the switch 37. The optimum DC value-calculating unit 33 connected with the amplifier 32 calculates the optimum DC force to be generated by the electromagnetic force generator. The calculated force is sent to the DC voltage generator 35 via the switch 34. It is further sent to the adder 36, where the force is added to the AC current. The adder 36 is connected with the coil 7. The DC signal which is produced from the adder 36 and on which the AC current is superimposed is converted into a DC force on which the AC current is superimposed, the DC force being applied to the sample 1 and to the leaf springs 9 via the detection rod 6 from the coil 7. Because of the above-described negative feedback control over the detector support 12, the DC force on which the AC current is superimposed is added to the sample 1. On the other hand, only the AC force is applied to the leaf springs 9; no DC force is applied.

The AC force applied to the sample 1 and to the leaf springs 9 produces AC-like strain in them. This AC strain is detected by the linear variable differential transformer 11 and converted into digital form via the strain-measuring circuit 40, the high-pass filter 45, and the analog-to-digital converter 46. The digital signal is then sent to the Fourier-calculating unit 47. The Fourier-calculating unit 47 calculates the amplitude of the AC strain produced in the sample 1 and in the leaf springs 9 simultaneously according to the following calculations (Math. 1):

[Math. 1]

$$a = (2/N)\sum_{i=1}^{N} x_i \cos(2\pi i/N)$$

$$b = (2/N)\sum_{i=1}^{N} x_i \sin(2\pi i/N)$$

Amplitude of AC Strain: $(a^2+b^2)^{1/2}$ where N is the number of division, i is a data number, π is the ratio of the circumference of a circle to its diameter, and x is a strain signal.

The measured value of the strain amplitude is sent to the strain amplitude controller 49 and compared with the target value of the strain amplitude sent from the target strain amplitude input device 50. Thus, the next gain of the amplifier 32 is determined. As a result of the strain amplitude control provided thus far, the amplitude of the AC strain produced in the sample 1 is always controlled so as to approach the target value set by the operator.

The sinusoidal wave alternating current produced by the amplifier 32 is converted into digital form by the analog-to-digital converter 48 and then sent to the Fourier-calculating unit 47. This calculating unit 47 calculates the AC stresses produced in the sample 1 and in the leaf springs 9, the ratio of the amplitudes of the alternating strains, and the phase difference by the following calculations (Math. 2):

[Math. 2]

$$A = (2/N)\sum_{i=1}^{N} F_i \cos(2\pi i/N)$$

$$B = (2/N)\sum_{i=1}^{N} F_i \sin(2\pi i/N)$$

Amplitude Ratio: $(A^2+B^2)^{1/2}/(a^2+b^2)^{1/2}$

Phase Difference: (Ab−Ba)/(Aa+Bb), F: force signal

Information about the amplitude ratio and phase difference obtained by the Fourier-calculating unit 47 is sent to a dynamic viscoelasticity-calculating unit 51, which in turn determines the dynamic viscoelasticity of the sample 1 by the following calculations (Math. 3):

[Math. 3]

storage Elastic Modulus=(L/S)×[amplitude ratio×cos (phase difference)−K]

Loss Elastic Modulus=(L/S)×[amplitude ratio×sin (phase difference)]

where L is the length of the sample, S is the cross-sectional area of the sample, and K is the elastic coefficient of the leaf springs.

Information about the dynamic viscoelasticity of the sample 1 obtained by the dynamic viscoelasticity-calculating unit 51 is stored in a storage device 54. Of course, the information can be produced to a recording means such as a printer (not shown) or a CRT (not shown) or a display means.

The following description centers on the difference with the aforementioned sinusoidal wave measurement where the operator selects measurement using composite waves.

Figure 2:
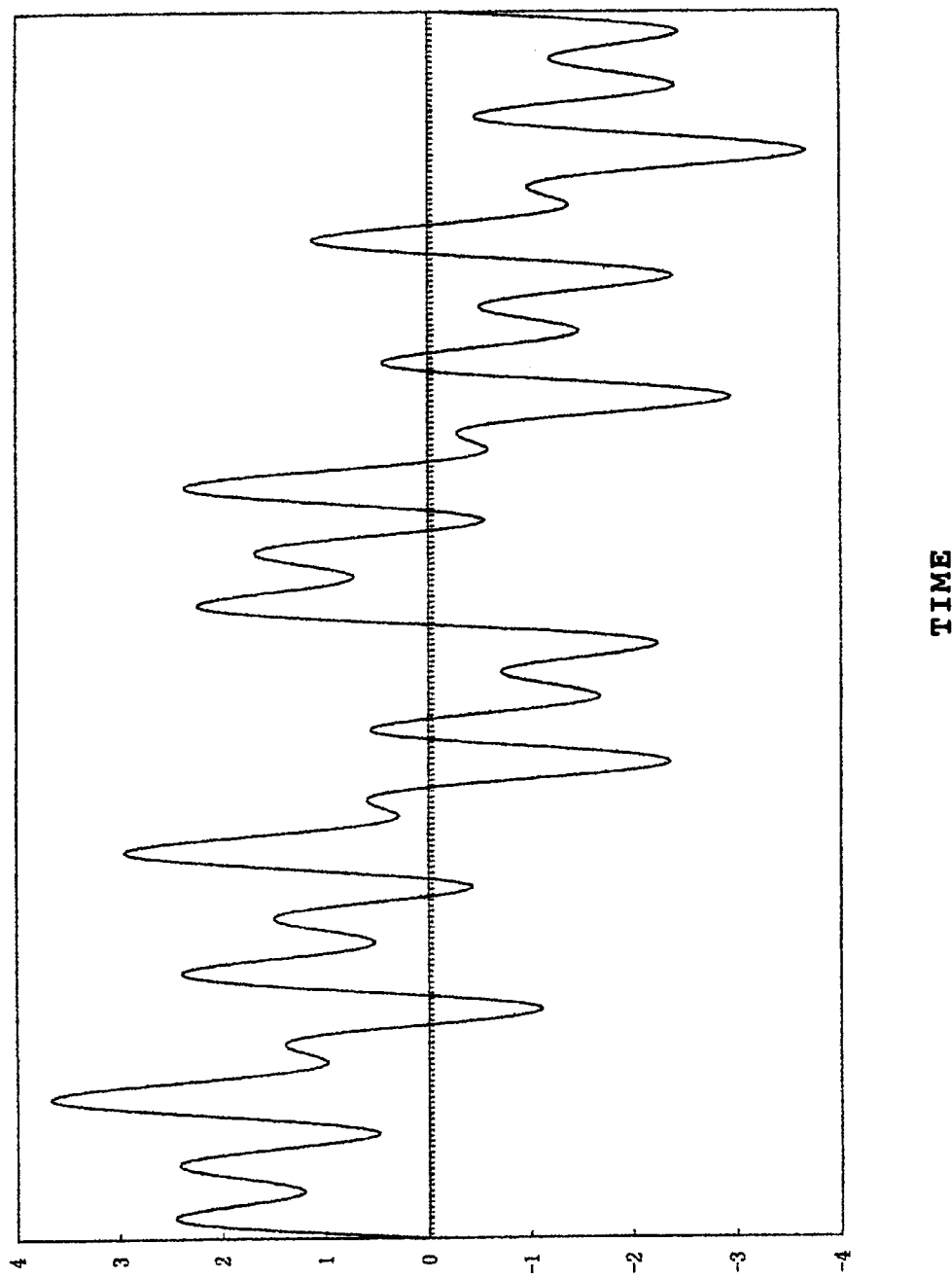
FIG. 2 is a diagram illustrating the waveform of one period of a composite wave used in the embodiment.
Figure 3A:
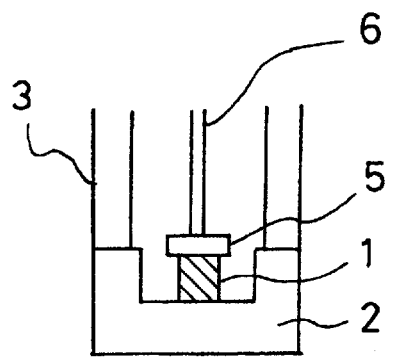
FIGS. 3a–3e show various cross sections illustrating various methods of holding samples.
Figure 3B:
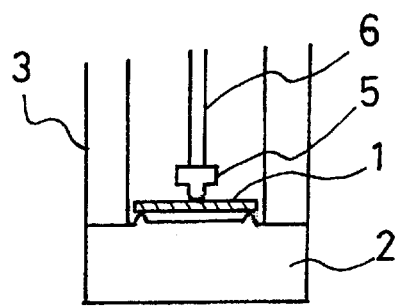
Figure 3C:
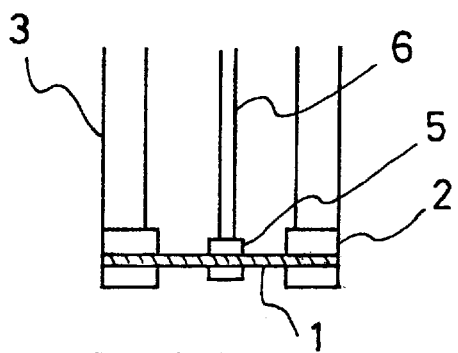
Figure 3D:
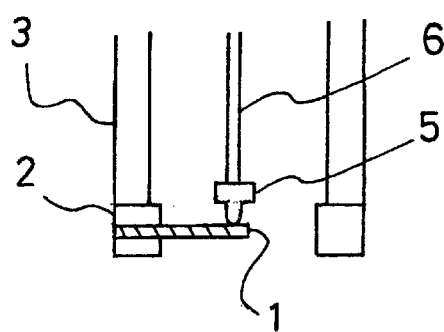
Figure 3E:
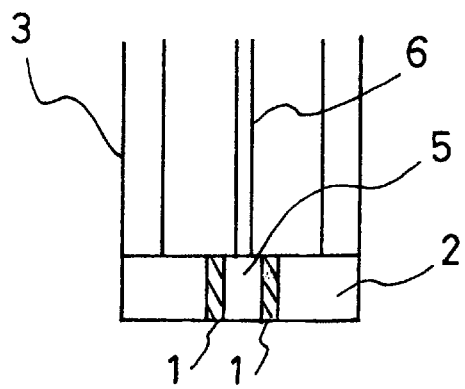

Composite waves used by the present inventors and others are each a waveform that is a fundamental sinusoidal wave as shown in FIG. 2 on which its double, quadruple, ten-fold, and twenty-fold waves of equal amplitude are superimposed. Prior to measurement, the operator sets one fundamental sinusoidal wave frequency of the composite wave between 0.01 Hz and 5 Hz instead of setting the frequencies of the sinusoidal waves described above. The other conditions are set in exactly the same way as in the case of sinusoidal waves.

The operation of the instrument during measurement is slightly different from the case of sinusoidal wave measurement in that only the amplitude of the fundamental wave is under strain-amplitude control. In composite wave measurement mode, the Fourier-calculating unit 47 calculates the stress-strain amplitude ratios and the phase differences about the fundamental, double, quadruple, tenth-fold, and twenty-fold waves as follows:

[Math. 4]

$$Aj = (2/N)\sum_{i=1}^{N} F_i \cos(2\pi ij/N)$$

$$Bj = (2/N)\sum_{i=1}^{N} F_i \sin(2\pi ij/N)$$

$$aj = (2/N)\sum_{i=1}^{N} x_i \cos(2\pi ij/N)$$

$$bj = (2/N)\sum_{i=1}^{N} x_i \sin(2\pi ij/N)$$

Amplitude Ratio: $(Aj^2+Bj^2)^{1/2}/(aj^2+bj^2)^{1/2}$

Phase Difference: (Ajbj−Bjaj)/(Ajaj+Bjbj)

j: magnifications (1, 2, 4, 10, and 20) relative to the fundamental frequency

Accordingly, the dynamic viscoelasticity-calculating unit 51 determines the dynamic viscoelasticities of the sample 1 for all the five frequencies by the same procedure as in the case of sinusoidal wave measurement.

Therefore, the information efficiency per unit time is superior to sinusoidal wave measurement. However, the frequency components are limited to the amplitudes of one-fifth of the upper limit of the force generated by the electromagnetic force generator. This produces the disadvantage that the range of measured elastic modulus is narrower than sinusoidal waves.

The operation of the instrument when the operator selects creep measurement mode is next described.

In the case of creep measurement, the temperature of the sample 1 is kept constant by the action of the temperature controller 55 and the heat-and-cooling furnace 20.

If the creep measurement is selected, the switches 34 and 37 are opened, so that the AC signal produced by the AC function generator 31 is no longer sent to the coil 7. The switch 43 connects the strain potential control circuit 42 with the stepping motor driver circuit 39. The switch 44 connects the function generator 38 with the DC voltage generator 35. The operator starts a measurement after entering a rectangular wave function into the function generator 38.

The rectangular wave generated by the function generator 38 is sent to the coil 7 via the DC voltage generator 35 and via the adder 36. The rectangular wave force produced by the coil 7 is transmitted to the sample 1 and to the leaf springs 9 via the detection rod 6. The strain produced in them is detected by the linear variable differential transformer 11. The strain signal detected by the linear variable differential transformer 11 is sent to the stepping motor driver circuit 39 via the strain-measuring circuit 40, the low-pass filter 41, and the strain potential control circuit 42, in the same way as in the case of sinusoidal wave measurement. This drives the stepping motor 16, moving the detector support 12 up and down. Finally, the output from the linear variable differential transformer 11 is always brought close to zero. At this time, the leaf springs 9 are relieved from strain and so the output from the coil 7 is fully applied to the sample 1. The amount of movement of the detector support 12 made by the operation of the stepping motor 16 is coincident with the amount of deformation of the sample 1.

Accordingly, the output from the DC voltage generator 35 is converted into digital form by the analog-to-digital converter 52 and sent to the static viscoelasticity-calculating unit 53. The output from the stepping motor driver circuit 39 is converted into digital form by the analog-to-digital converter 56 and fed to the static viscoelasticity-calculating unit 53. Thus, the viscoelasticity-calculating unit 53 can compute the stress in the sample 1 from the former value and the strain in the sample 1 from the latter value according to the following formulas:
[Math. 5]

stress=DC force/S strain=amount of movement of detector support 12/L
where S is the cross-sectional area of the sample and L is the length of the sample.

That is, the static viscoelasticity-calculating unit 53 can obtain data from creep restoration measurements that are strain response of the sample 1 to rectangular wave stress, and can measure the static viscoelasticity of the sample.

Then, the operation of the instrument when the operator selects stress relaxation measurement mode is described.

Also, in the stress relaxation measurement, the temperature of the sample 1 is kept constant by the action of the temperature controller 55 and the heating-and-cooling furnace 20, in the same way as in the case of creep measurement.

If stress relaxation measurement is selected, the switches 34 and 37 are opened, so that the AC signal generated by the AC function generator 31 is no longer sent to the coil 7. The switch 43 connects the strain potential control circuit 42 with the DC voltage generator 35. The switch 44 connects the function generator 38 with the stepping motor driver circuit 39. After entering a rectangular wave function into the function generator 38, the operator starts a measurement.

The rectangular wave produced by the function generator 38 is sent to the stepping motor 16 by way of the stepping motor driver circuit 39. Movement of the stepping motor 16 moves the detector support 12 like rectangular waves. At this time, the total amount of movement of the detector support 12 is distributed to deformation of the sample 1 and to deformation of the leaf springs 9. Only the strain induced in the leaf springs 9 is detected by the linear variable differential transformer 11. The strain signal detected by the linear variable differential transformer 11 is fed to the strain potential control circuit 42 via the strain-measuring circuit 40 and via the low-pass filter 41. The strain potential control circuit 42 calculates the DC force to be generated by the coil 7 according to proportional control to bring the low-frequency component of the measured strain close to zero. Then, the calculated DC force signal is sent to the DC voltage generator 35 via the switch 43. The whole instrument provides negative feedback control for varying the DC force generated by the electromagnetic force generator to return the output from the linear variable differential transformer 11 to zero at all times. At this time, the leaf springs 9 are relieved from strain and so the output from the coil 7 is totally applied to the sample 1. The amount of movement of the detector support 12 made by the operation of the stepping motor 16 agrees with the amount of deformation of the sample 1.

The output from the DC voltage generator 35 is converted into digital form by the analog-to-digital converter 52 and sent to the static viscoelasticity-calculating unit 53. The output from the stepping motor driver circuit 39 is converted into digital form by the analog-to-digital controller 56 and sent to the static viscoelasticity-calculating unit 53. Accordingly, the static viscoelasticity-calculating unit 53 can calculate the stress in the sample 1 from the former value, in exactly the same way as in the case of creep measurement.

That is, the static viscoelasticity-calculating unit 53 can obtain data about stress relaxation measurements that are stress response of the sample 1 to rectangular wave strains. The static viscoelasticity of the sample can be measured.

The results of creep measurements and stress relaxation measurements are sent from the static viscoelasticity-calculating unit 53 to the storage device 54, where the results are stored. Besides, the results can be produced to a recording means or a display means such as a printer (not shown) or CRT (not shown).

The description of the embodiments provided thus far is based on the sample-gripping structure for tensile measurement shown in FIG. 1.

However, using a sample-holding structure as shown in FIG. 3, the instruments of the embodiments can be measured in various deformation modes such as compression, three-point bending, dual cantilever, single cantilever, and shear. In measurements under various deformation conditions such as dual cantilever and shear, the requirement that the sign of force be not reverse during measurement (i.e., the DC force must be always in excess of the amplitude of the AC force) is made unnecessary unlike the tensile case. Therefore, measurements are made under conditions where the switch 34 is opened and the DC force is not superimposed. In quantifying the viscoelasticity, the sample shape is handled partially differently. Other conditions and the operation of the instrument are exactly the same as in the case of the aforementioned tensile measurement.

A part of the analog signal-processing portion of the present embodiment may be formed as a digital-processing portion, and the signals may be processed by a processor. Conversely, a part of the digital signal-processing portion may be an analog signal-processing portion, as a matter of course.

Data measured by the instruments given in the illustrative embodiments are hereinafter described.

FIG. 4 shows the dynamic viscoelasticity of thin sheets of PMMA (polymethyl methacrylate). The viscoelasticity was measured with a composite wave having a fundamental frequency of 0.5 Hz. The sample was heated at a rate of 4 degrees per minute. A large drop of the storage modulus (E')

and peaks of loss modulus (E") and of loss tangent (tan delta) were observed near 130 degrees. At the same time, frequency dispersion between 0.5 and 10 Hz was confirmed.

Figure 5:
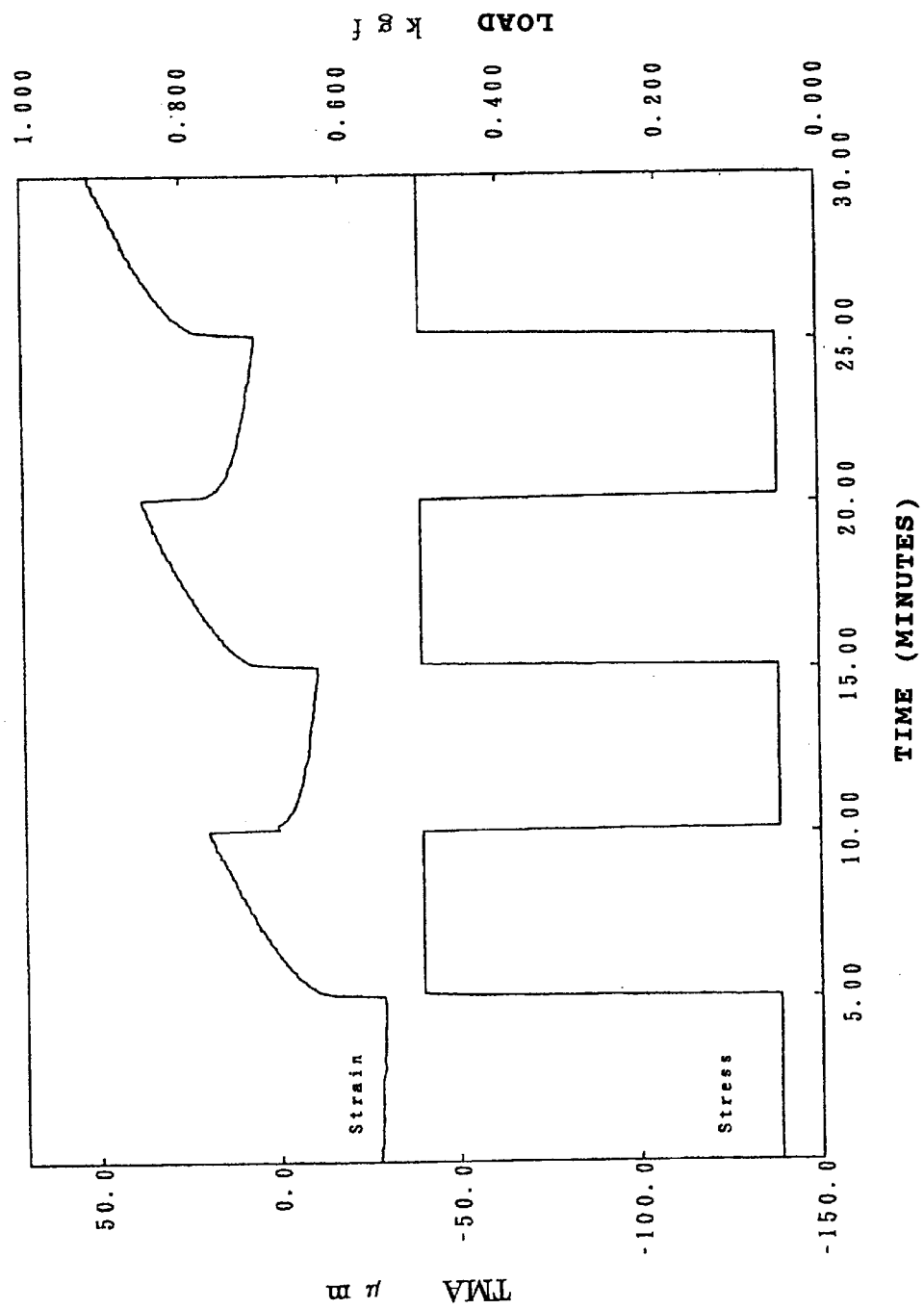
FIG. 5 is data obtained by measuring creep restoration characteristics of PMMA at 115 degrees.

FIG. 5 shows measurement of creep restoration characteristics of PMMA at 115 degrees. The load was switched between 50 g and 500 g at intervals of 5 minutes. The resulting deformation, or distortion, was measured. The manner in which the creep of the PMMA was restored at this temperature was known.

Figure 6:
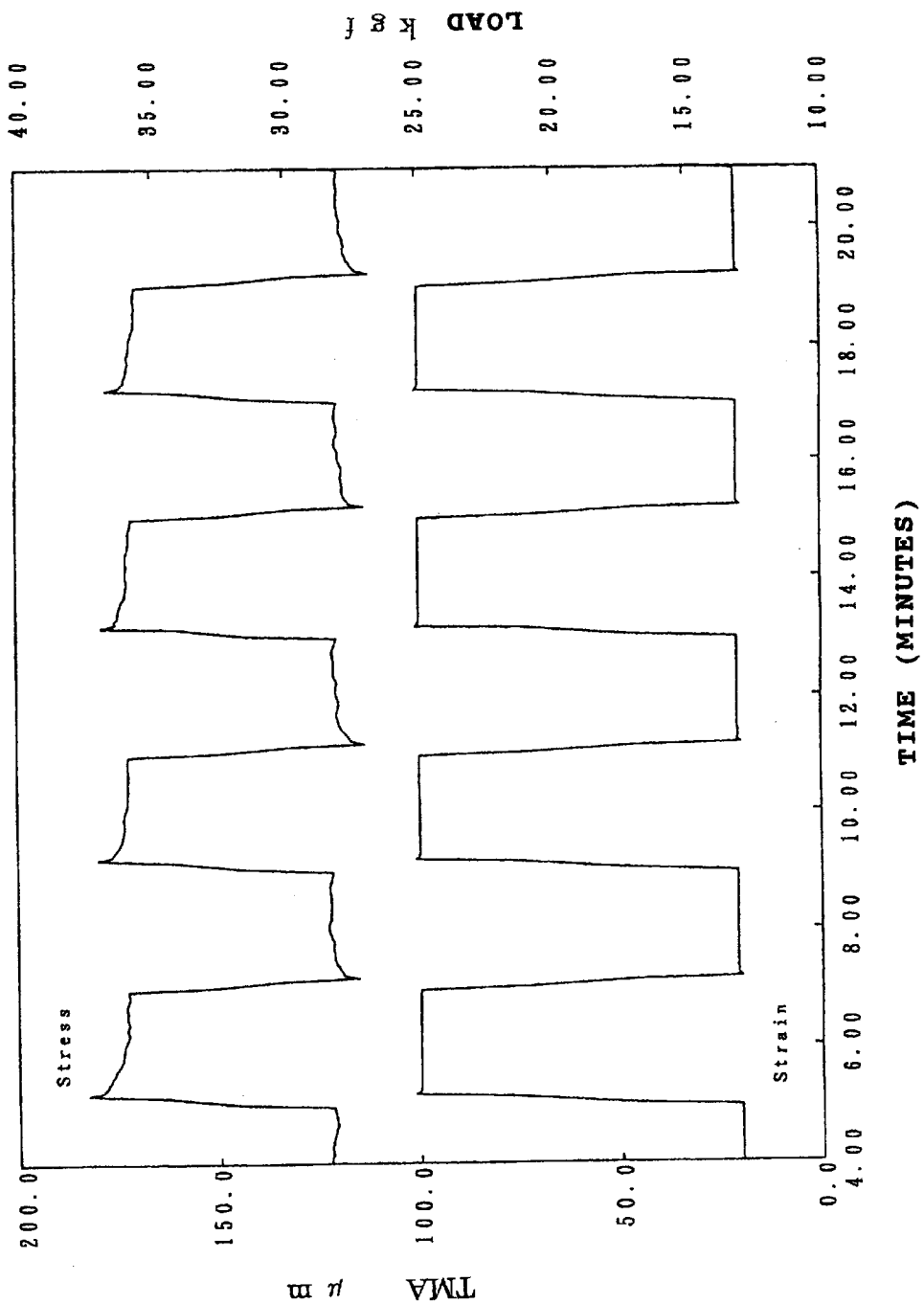
FIG. 6 is data obtained by measuring the stress relaxation characteristics of PMMA at 140 degrees.

FIG. 6 shows measurement of the stress relaxation characteristics of the PMMA at 140 degrees. The amount of distortion was varied by 4% into rectangular wave at intervals of 2 minutes. Variations of the stress were sensed. After variation of the stress, the PMMA sample relaxed. Concomitantly, the stress was observed to decrease.

As described thus far, in accordance with the present invention, a detection rod that is a means for transmitting force to a sample and simultaneously is a means for transmitting deformation of the sample is held by leaf springs. In spite of this, negative feedback control is provided to return the deformation of the leaf springs to zero at all times. Thus, it is easy to separate the spring constant effect of the leaf springs. The dynamic viscoelasticity of a material can be measured within a range of from 0.01 Hz to 100 Hz. In addition, static viscoelasticities such as creep restoration and stress relaxation can be measured. In this way, the viscoelastic characteristics of a material can be analyzed from various aspects. Since the average displacement of the leaf springs is zero, the positional relation between the permanent magnet and the coil forming the electromagnetic force generator hardly varies. Therefore, the linearity between the current flowing through the coil and the generated force is secured well. This enhances the accuracy of the measured data about viscoelasticity.

What is claimed is:

1. A viscoelasticity measurement apparatus comprising:
   a sample holder for supporting at least one end of a sample;
   a sample chuck for supporting a part of the sample independently of the sample holder;
   a detector support capable of moving relative to the sample holder;
   a detection rod coupled to the sample chuck and elastically held to the detector support;
   a displacement detector for sensing variations in a longitudinal position of the detection rod relative to the detector support and producing a corresponding output signal;
   a force generator fixedly mounted to the detector support for applying a longitudinal force to one end of the detection rod to thereby apply stress to the sample via the detection rod and via the sample chuck;
   a program function generator connected with the force generator and capable of establishing a target function of the stress to be applied to the sample with respect to time;
   feedback control means for varying position of the detector support relative to the sample holder so that the output signal of the displacement detector approaches zero;
   recording means for recording the output from the force generator and the amount of movement of the detector support relative to the sample holder; and
   a static viscoelasticity calculating unit for determining a static stress applied to the sample based on the output of the force generator, a static strain produced in the sample based on the amount of movement of the detector support relative to the sample holder, and calculating the static viscoelasticity of the sample based on a relation between the static stress applied to the sample and the static strain produced in the sample.

2. A viscoelasticity measurement apparatus comprising:
   a sample holder for supporting at least one end of a sample;
   a sample chuck for supporting a part of the sample independently of the sample holder;
   a detector support capable of moving relative to the sample holder;
   a detection rod coupled to the sample chuck and elastically held to the detector support;
   a displacement detector for sensing variations in a longitudinal position of the detection rod relative to the detector support and producing a corresponding output signal;
   a force generator fixedly mounted to the detector support for applying a longitudinal force to one end of the detection rod to thereby apply stress to the sample via the detection rod and via the sample chuck;
   a DC current generator for producing a DC signal to cause the force generator to deliver a force to the sample;
   a program function generator capable of setting a target value of an amount of movement of the detector support relative to the sample holder with respect to time;
   a feedback control circuit for varying an output of the DC generator so that the output of the displacement detector approaches zero;
   recording means for recording the output of the force generator and the amount of movement of the detector support relative to the sample holder; and
   a static viscoelasticity calculating unit for determining a static stress applied to the sample based on the output of the force generator, a static strain produced in the sample based on the amount of movement of the detector support relative to the sample holder, and calculating a static viscoelasticity of the sample based on a relation between the static stress applied to the sample and the static strain produced in the sample.

3. A viscoelasticity measurement apparatus comprising:
   a sample holder for supporting at least one end of a sample;
   a sample chuck for supporting a part of the sample independently of the sample holder;
   a detector support capable of moving relative to the sample holder;
   a detection rod coupled to the sample chuck and elastically held to the detector support;
   a displacement detector for sensing variations in a longitudinal position of the detection rod relative to the detection support and producing a corresponding output;
   a force generator fixedly mounted to the detection support and acting to apply a longitudinal force to one end of the detection rod to thereby apply stress to the sample via the detection rod and via the sample chuck;
   a DC current generator for producing a DC signal to cause the force generator to deliver a non-periodic force to the sample;
   a periodic function generator for producing a periodic function signal to cause the force generator to deliver a periodic force to the sample;

feedback control means for varying the position of the detector support relative to the sample holder so that an average output of the displacement detector approaches zero;

recording means for recording the DC output of the force generator and the amount of movement of the detector support relative to the sample holder;

an arithmetic unit for Fourier-transforming frequency function components of the periodic function signal output by the periodic function generator and periodic function components of a displacement signal sensed by the displacement detector; and a viscoelasticity calculating unit for determining a static stress applied to the sample by the force generator, a static strain produced in the sample based on the amount of movement of the detector support relative to the sample holder, calculating a static viscoelasticity of the sample based on a relation between the static stress applied to the sample and the amount of movement of the detector support relative to the sample holder, and calculating dynamic viscoelasticity of the sample.

4. The viscoelasticity measurement apparatus of claim 3; wherein the periodic function generator alternates generation and cessation of the periodic function signal, and wherein the feedback control means operates only during the cessation period.

5. The viscoelasticity measurement apparatus of claim 3; wherein the periodic function generated by the periodic function generator is a composite wave function obtained by summing up sinusoidal waves having different frequencies, and wherein the arithmetic unit can deliver dynamic viscoelasticity values of the sample corresponding to frequencies of the sinusoidal waves.

6. A viscoelasticity measurement apparatus according to claim 1; wherein the program function generator produces a signal having at least one of a DC component and an AC component representative of a stress to be applied to the sample.

7. A viscoelasticity measurement apparatus according to claim 6; wherein the feedback control means varies a DC component of a signal produced by the program function generator to vary the position of the detector support relative to the sample holder so that the output signal of the displacement detector approaches zero.

8. A viscoelasticity measurement apparatus according to claim 1; wherein the program function generator includes a DC current generator for producing a DC signal to cause the force generator to deliver a non-periodic force to the sample; and the feedback control means varies an output of the DC current generator so that the output of signal of the displacement detector approaches zero.

9. A viscoelasticity measurement apparatus according to claim 1; wherein the program function generator includes a DC current generator for producing a DC signal to cause the force generator to deliver a non-periodic force to the sample; and the feedback control means includes means for moving the detector support relative to the sample holder so that the output signal of the displacement detector approaches zero.

10. A viscoelasticity measurement apparatus according to claim 1; wherein the program function generator comprises a DC current generator for producing a DC signal to cause the force generator to deliver a non-periodic force to the sample and a periodic function generator for producing a periodic signal to cause the force generator to deliver a periodic force to the sample; and the feedback control means varies an output of the DC generator so that the output signal of the displacement detector approaches zero.

11. A viscoelasticity measurement apparatus comprising: a sample holder for supporting one end of a sample; a sample chuck for supporting another end of the sample independently of the sample holder; a detector support capable of moving relative to the sample holder; a detection rod coupled at one end to the sample chuck and elastically held to the detector support; a displacement detector for detecting variations in a longitudinal position of the detection rod relative to the detector support and producing a corresponding output signal; a force generator fixedly mounted to the detector support for applying a longitudinal force to one end of the detection rod to thereby apply at least one of a compressive stress and a tensile stress to the sample via the detection rod and the sample chuck; a function generator connected with the force generator for outputting a signal to the force generator for applying a stress to the sample; a feedback circuit for varying the position of the detector support relative to the sample holder so that the output of the displacement detector approaches zero; and a static viscoelasticity calculating unit for determining a static viscoelasticity of the sample based on the stress applied to the sample by the force generator and strain produced by the sample and detected by movement of the detector support relative to the sample holder.

12. A viscoelasticity measurement apparatus according to claim 11; further comprising springs for elastically supporting the detection rod to the detector support.

13. A viscoelasticity measurement apparatus according to claim 11; further comprising recording means for recording the output of the force generator and the amount of movement of the detector support relative to the sample holder.

14. A viscoelasticity measurement apparatus according to claim 11; further comprising a DC current generator for producing a DC signal to cause the force generator to deliver a non-periodic force to the sample; wherein the feedback circuit varies an output of the DC generator so that the output of the displacement detector approaches zero.

15. A viscoelasticity measurement apparatus according to claim 11; further comprising a DC current generator for producing a DC signal to cause the force generator to deliver a non-periodic force to the sample and a periodic function generator for producing a periodic signal to cause the force generator to deliver a periodic force to the sample, and an arithmetic unit for Fourier-transforming frequency components of the periodic function signal output by the periodic function generator and periodic components of a displacement signal sensed by the displacement detector and determining the dynamic viscoelasticity of the sample as a result of calculation; wherein the feedback circuit varies the position of the detector support relative to the sample holder so that average output of the displacement detector approaches zero.

16. A viscoelasticity measurement apparatus according to claim 15; wherein the recording means records the DC output of the force generator.

17. A viscoelasticity measurement apparatus according to claim 15; wherein the periodic function generator alternates generation and cessation of the periodic signal, and the feedback control circuit operates only during the cessation period.

18. A viscoelasticity measurement apparatus according to claim 15; wherein the periodic function generated by the periodic function generator is a composite wave function obtained by summing up sinusoidal waves having different frequencies, and the arithmetic unit determines dynamic viscoelasticity values of the sample corresponding to the different frequencies of the sinusoidal waves.

19. A viscoelasticity measurement apparatus comprising: a sample holder for supporting at least one end of a sample; a sample chuck for supporting another end of the sample; a detector support capable of relative movement with respect to the sample holder; a force applying member coupled to the sample chuck; a support member for elastically connecting the force applying member to the detector support; a displacement detector for detecting variations in position of the force applying member relative to the detector support and outputting a corresponding signal; a function generator for producing a signal having at least one of a DC component and an AC component representative of a stress to be applied to the sample; a force generator fixedly mounted to the detector support for applying a force to the force applying member to apply stress to the sample in accordance with the signal produced by the function generator; and one of mechanical feedback means for varying the position of the detector support relative to the sample holder and electrical feedback means for varying a DC component of the signal output by the function generator, so that a DC component of the output signal of the displacement detector approaches zero.

20. A viscoelasticity measurement apparatus according to claim 19; wherein the electrical feedback means comprises a negative feedback control circuit for varying a DC output of the force generator so that the DC component of the output signal of the displacement detector approaches zero.

21. A viscoelasticity measurement apparatus according to claim 19; wherein the detector support is mounted on a bearing and driven by a stepper motor to move the detector support relative to the sample holder.

22. A viscoelasticity measurement apparatus according to claim 19; further comprising recording means for recording an output of the force generator and the amount of movement of the detector support relative to the sample holder.

23. A viscoelasticity measurement apparatus according to claim 19; further comprising a static viscoelasticity calculating unit for determines a static viscoelasticity of the sample based on the stress applied to the sample by the force generator and strain produced by the sample in response thereto and detected based on movement of the detector support relative to the sample holder.

24. A viscoelasticity measurement apparatus according to claim 19; further comprising an arithmetic unit for determining the Fourier-transform of periodic components of the signal output by the function generator and periodic components of a displacement signal detected by the displacement detector and determining the dynamic viscoelasticity of the sample in accordance therewith.

* * * * *